United States Patent [19]

Teutsch

[11] 4,147,695
[45] Apr. 3, 1979

[54] 11β-SUBSTITUTED-Δ⁹-STEROIDS

[75] Inventor: Jean G. Teutsch, Le Blanc-Mesnil, France

[73] Assignee: Roussel Uclaf, Paris, France

[21] Appl. No.: 867,484

[22] Filed: Jan. 6, 1978

[30] Foreign Application Priority Data

Jan. 13, 1977 [FR] France ................. 77 00857

[51] Int. Cl.² ............................................. C07J 21/00
[52] U.S. Cl. .................. 260/239.55 C; 260/239.5; 260/239.55 R; 260/397.45; 260/397.5
[58] Field of Search ................................ 260/340.9 AS

[56] References Cited

U.S. PATENT DOCUMENTS 2,880,233  3/1959  Clinton ................. 260/340.9 AS

FOREIGN PATENT DOCUMENTS 2237906  2/1975  France ................. 260/239.55 C

Primary Examiner—Ethel G. Love
Attorney, Agent, or Firm—Hammond & Littell

[57] ABSTRACT

Novel 11β-substituted-Δ⁹-ene-5α-ols of the formula

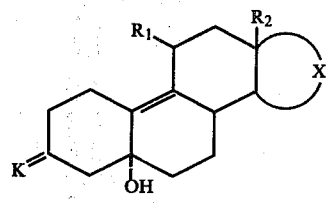

wherein K is a blocked ketone in the form of a ketal, thio-ketal or methyloxime, X is a pentagonal or hexagonal ring optionally substituted, $R_1$ is selected from the group consisting of branched and straight chain alkyl of 1 to 12 carbon atoms, unsaturated alkyl of 2 to 8 carbon atoms optionally substituted, optionally substituted aryl of 6 to 12 carbon atoms, optionally substituted aralkyl of 7 to 13 carbon atoms and heterocycle with at least one hetero oxygen or sulfur atom and $R_2$ is alkyl of 1 to 4 carbon atoms which are useful intermediates and a process for their preparation.

13 Claims, No Drawings

11β-SUBSTITUTED-Δ⁹-STEROIDS

STATE OF THE ART

U.S. Pat. No. 3,876,637 describes $\Delta^9$-5α-ol steroids and U.S. Pat. No. 3,872,092 describes $\Delta^{9,11}$-5α-ol steroids but they contain a different substituent in the 11β-position.

OBJECTS OF THE INVENTION

It is an object of the invention to provide the novel 11β-substituted-$\Delta^9$-steroids of formula I and to a novel process for the preparation of the compounds of formula I.

These and other objects and advantages of the invention will become obvious from the following detailed description.

THE INVENTION

The novel 11β-substituted steroids of the invention have the formula

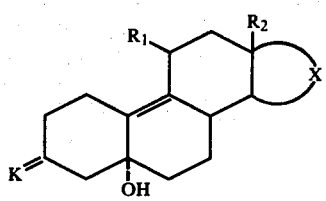

wherein K is a blocked ketone in the form of a ketal, thioketal or methyloxime, X is a pentagonal or hexagonal ring optionally substituted, $R_1$ is selected from the group consisting of branched and straight chain alkyl of 1 to 12 carbon atoms, unsaturated alkyl of 2 to 8 carbon atoms optionally substituted, optionally substituted aryl of 6 to 12 carbon atoms, optionally substituted aralkyl of 7 to 13 carbon atoms and heterocycle with at least one hetero oxygen or sulfur atoms and $R_2$ is alkyl or 1 to 4 carbon atoms.

Examples of $R_1$ are alkyl such as methyl, ethyl, propyl, isopropyl, butyl, isobutyl, tert.-butyl, n-pentyl, n-hexyl, 2-methyl-pentyl, 2,3-dimethyl-butyl, n-heptyl, 2-methyl-hexyl, 2,2-dimethylpentyl, 3,3-dimethylpentyl, 3-ethylpentyl, n-octyl, 2,2-dimethylhexyl, 3,3-dimethylhexyl, 3-methyl-3-ethylpentyl, nonyl, 2,4-dimethylheptyl and n-decyl; unsaturated alkyl such as vinyl, isopropenyl, allyl, 2-methylallyl and isobutenyl; substituted unsaturated alkyl, preferably with an alkoxy such methoxy or ethoxy or with a thioalkyl such as thiomethyl or thioethyl or one or more halogens such as fluorine atoms, aryl and aralkyl such as phenyl or benzyl optionally substituted in the o-, m- or p-positions with at least one member of the group consisting of alkyl of 1 to 4 carbon atoms, alkoxy of 1 to 4 carbon atoms such as methoxy, halogens such as chlorine or fluorine and —$CF_3$; and heterocycles such as thienyl, isothienyl and furyl.

Examples of $R_2$ are alkyl such as methyl, ethyl or propyl. Preferably K is a ketal such as ethyleneketal.

Particularly preferred compound of formula I are those wherein X is a pentagonal ring and the compounds have the formula

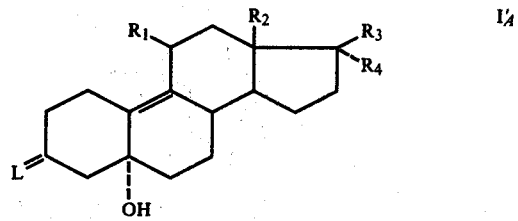

wherein $R_1$ and $R_2$ have the above definition, L is a ketal and either $R_3$ is selected from the group consisting of hydrogen, hydroxy, acyloxy of an organic carboxylic acid of 1 to 18 carbon atoms, alkoxy of 1 to 8 carbon atoms and acyl of an organic carboxylic acid of 1 to 18 carbon atoms and $R_4$ is selected from the group consisting of hydrogen, hydroxy, alkyl and alkoxy of 1 to 8 carbon atoms, alkenyl and alkynyl of 2 to 8 carbon atoms, acyloxy of an organic carboxylic acid of 1 to 18 carbon atoms and cyano or one of $R_3$ and $R_4$ is a blocked hydroxy in the form of an easily removable ether and the other is cyano or together from a ketone optionally protected as a cyclic ketal. L is preferably a cyclic alkylketal of 2 to 4 carbon atoms such as ethyleneketal or propyleneketal or a dialkylketal such as dimethylketal or diethylketal. When $R_3$ and $R_4$ are a ketone protected in the form of a cyclic ketal, it is preferably a cyclicketal of 2 to 4 carbon atoms such as ethyleneketal or propyleneketal.

Examples of $R_3$ and $R_4$ are alkoxy such as methoxy, ethoxy, propoxy, isopropoxy, pentyloxy, isopentyloxy and tert butoxy; acyl or acyloxy of an organic carboxylic acid of 1 to 18 carbon atoms such as alkanoic acids such as formic acid, acetic acid, propionic acid, butyric acid, isobutyric acid or undecylic acid; hydroxyalkanoic acids such as hydroxyacetic acid; cycloalkylcarboxylic acids and cycloalkylalkanoic acids such as cyclopropylcarboxylic acid, cyclobutylcarboxylic acid, cyclopentylcarboxylic acid, cyclohexylcarboxylic acid, cyclopentylacetic acid, cyclohexylacetic acid, cyclopentylpropionic acid or cyclohexylpropionic acid; benzoic acid; phenylalkanoic acids such as phenylacetic acid or phenylpropionic acid; or amino acids such as diethylaminoacetic acid or aspartic acid.

Further examples of $R_4$ are alkyl such as methyl, ethyl, propyl or butyl; alkenyl such as vinyl, allyl, 2-methyl-allyl or isobutenyl; and alkynyl such as ethynyl, 1-propynyl, 2-propynyl, 2-butynyl or butadiynyl.

Among the preferred compounds of formula I are those wherein $R_2$ is methyl or ethyl, those wherein $R_1$ is straight or branched chain alkyl of 1 to 12 carbon atoms, those wherein $R_1$ is branched or straight chain alkenyl or alkynyl of 2 to 4 carbon atoms optionally substituted with alkoxy or alkylthio of 1 to 4 carbon atoms or one or more fluorine atoms especially vinyl, those wherein $R_1$ is phenyl or benzyl optionally substituted on the phenyl with one or more halogens, alkoxy or alkyl of 1 to 4 carbon atoms or —$CF_3$ or a combination thereof, those wherein $R_1$ is thienyl, those wherein $R_3$ is benzoyloxy and $R_4$ is hydrogen and those wherein $R_3$ is cyano and $R_4$ is trimethylsilyoxy.

The novel process of the invention for the preparation of compounds of formula I comprises reacting a compound of the formula

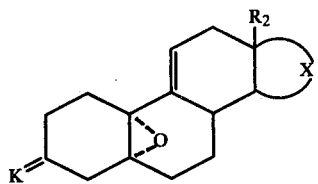

wherein K, $R_2$ and X have the above definitions with a compound of a formula selected from the group consisting of $(R_1)_2$ CuLi, $R_1$MgHal and $R_1$Li wherein $R_1$ has the above definition and Hal is a halogen in the presence of a catalytic amount of a cuprous halide when $R_1$MgHal and $R_1$Li are used.

Among the preferred compounds of formula II are those of the formula

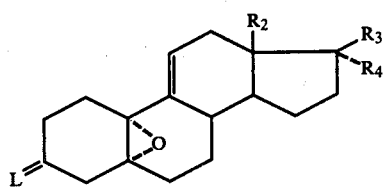

wherein L, $R_2$, $R_3$ and $R_4$ have the above definitions.

When the compound reacted with the compound of formula II is $(R_1)_2$ LiCu, the process is preferably effected at $-100°$ to $0°$ C. and when the reactant is $R_1$MgHal, the halogen is preferably chlorine or bromine and the catalyst is cuprous bromide or cuprous chloride and the reaction temperature is $-40°$ to $0°$ C. When the reactant is $R_1$Li, the catalyst is preferably cuprous bromide or cuprous chloride and the reaction temperature is $-40°$ to $0°$ C. Preferably the reaction is effected in an organic solvent or mixtures thereof such as ether, isopropyl ether and tetrahydrofuran.

The cuprous halide is eventually used in the form of a complex with dialkyl sulfid.

In a preferred mode of the invention, when $R_1$ is other than allyl or tert.-butyl, the 11$\beta$-substituent is introduced with $R_1$MgBr in the presence of a catalytic amount of cuprous chloride and the reaction is effected at $-40°$ to $-20°$ C. in ether and/or tetrahydrofuran. When $R_1$ is allyl or tert.-butyl, the 11$\beta$-substituent is introduced with $(R_1)_2$ CuLi at $-90°$ to $-10°$ C.

Also a preferred embodiment of the process of the invention to obtain a compound of formula I wherein $R_3$ is —OH and $R_4$ is ethynyl comprises reacting a compound of the formula

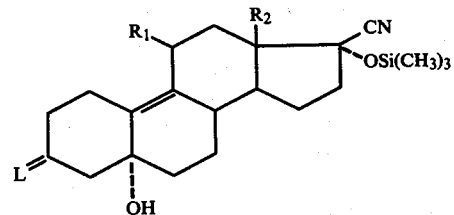

wherein L, $R_1$ and $R_2$ have the above definition with a lithium acetylide-ethylenediamine complex to obtain a compound of the formula

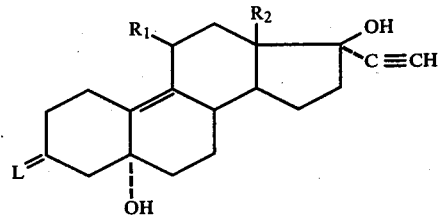

The starting compounds of formula II are generally known compounds and may be prepared as described in French Pat. No. 1,550,974 wherein a derivative of 3-ketal-13$\beta$-alkyl-$\Delta^{5(10),9(11)}$-gonadiene is reacted with an epoxidation agent such as peracid like peracetic acid, perphthalic acid or meta-chloroperbenzoic acid or by the process of French Pat. No. 2,201,287 wherein a derivative of 3-ketal-$\Delta^{5(10),9(11)}$-gonadiene is reacted with hexafluoroacetone hydroperoxide to obtain the corresponding 3-ketal-5$\alpha$,10$\alpha$-epoxy-$\Delta^{9(11)}$-gonene or by the process of French Pat. No. 2,082,129.

The compounds of formula I are useful as intermediates for the preparation of therapeutically active compounds such as by the processes described in commonly assigned application Ser. No. 867,486, filed on even date herewith, and Ser. No. 867,485, filed on even date herewith, by reacting a compound of formula I with a dehydration agent capable of liberating the ketone function such as sulfonic acid resins to obtain a compound of the formula

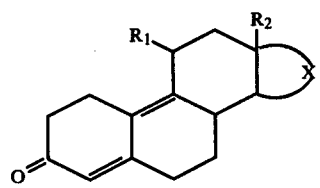

reacting the latter with an aromatization agent such as acetyl bromide with acetic anhydride to obtain a compound of the formula

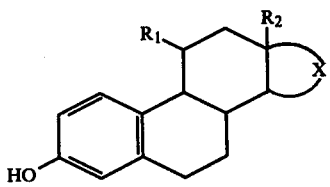

The compounds of formula III have progestomimetic activity and the compounds of formula IV have estrogenic activity.

In a preferred modification of the said process, a compound of the formula

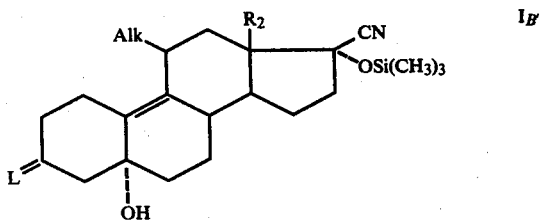

wherein L and $R_2$ have the above definition and Alk is alkyl of 1 to 12 carbon atoms is reacted with a lithium acetylideethylenediamine complex to obtain a compound of the formula

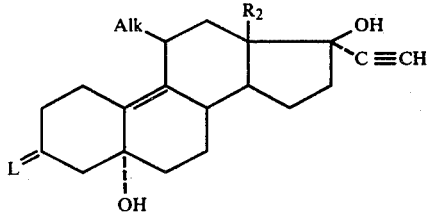

and reacting the latter with a deshydration agent capable of liberating the ketone function to obtain a compound of the formula

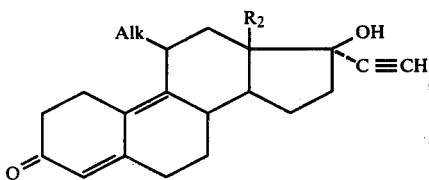

and reacting the latter with an aromatization agent to obtain a compound of the formula

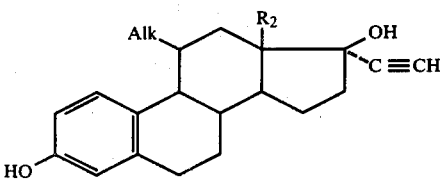

The 13β-alkyl compounds of formula IV$_B$, particularly the estrane series such as 11β-methyl-17α-ethynyl-Δ$^{1,3,5(10)}$-estratriene-3,17β-diol, are products well known to have estrogenic activity. The compounds of formula I$_B$, are useful for the preparation of compounds of formula IV$_B$ of the estrane series such as 11β-methyl-17α-ethynyl-Δ$^{1,3,5(10)}$-estratriene-3,17β-diol and is an object of the invention.

In the following examples there are described several preferred embodiments to illustrate the invention. However, it is to be understood that the invention is not intended to be limited to the specific embodiments.

EXAMPLE 1

5 mg of cuprous chloride were added to 1.1 ml of a solution of 1.17 M of phenyl magnesium bromide in tetrahydrofuran and after cooling the solution to −15° C., a solution of 430 mg of 3-[(1,2-ethanediyl)-acetal] of 5α,10α-epoxy-17α-trimethylsilyloxy-17β-cyano-Δ$^{9(11)}$-estrene-3-one in 2 ml of tetrahydrofuran was added. The mixture was stirred for 105 minutes at 0° C. and was then poured into an aqueous ammonium chloride solution. The mixture was extracted with ether and the ether extracts were dried and evaporated to dryness to obtain 503 mg of raw product which was crystallized from isopropyl ether to obtain 366 mg of 3-[(1,2-ethanediyl)-acetal] of 11β-phenyl-17α-trimethylsilyloxy-17β-cyano-Δ$^9$-estrene-5α-ol-3-one melting at 184° C.

EXAMPLE 2

Using the procedure of Example 1, propyl magnesium bromide was reacted with the said acetal to obtain a 60% yield of 3-[(1,2-ethanediyl)-acetal] of 11β-propyl-17α-trimethylsilyloxy-17β-cyano-Δ$^9$-estrene-5α-ol-3-one with a specific rotation of $[\alpha]_D^{20} = -58.5° \pm 2.5°$ (c=0.5% in ethanol).

EXAMPLE 3

Using the procedure of Example 1, isopropyl magnesium bromide was reacted with the said acetal to obtain 86% yield of 3-[(1,2-ethanediyl)-acetal] of 11β-isopropyl-17α-trimethylsilyloxy-17β-cyano-Δ$^9$-estrene-5α-ol-3-one with a specific rotation of $[\alpha]_D^{20} = -70° \pm 3°$ (c=0.5% in CHCl$_3$).

EXAMPLE 4

Using the procedure of Example 1, decyl magnesium bromide was reacted with the said acetal to obtain a 92% yield of 3-[(1,2-ethanediyl)-acetal] of 11β-decyl-17α-trimethylsilyloxy-17β-cyano-Δ$^9$-estrene-5α-ol-3-one with a specific rotation $[\alpha]_D^{20} = -42° \pm 1.5°$ (c=0.7% in CHCl$_3$).

EXAMPLE 5

Using the procedure of Example 1, vinyl magnesium bromide was reacted with the said acetal to obtain an 88% yield of 3-[(1,2-ethanediyl)-acetal] of 11β-vinyl-17α-trimethylsilyloxy-17β-cyano-Δ$^9$-estrene-5α-ol-3-one having a specific rotation of $[\alpha]_D^{20} = -60° \pm 2°$ (c=0.85% in CHCl$_3$) and melting at 213° C.

EXAMPLE 6

Using the procedure of Example 1, isopropenyl magnesium bromide was reacted with the said acetal to obtain a 78% yield of 3-[(1,2-ethanediyl)-acetal] of 11β-isopropenyl-17α-trimethylsilyloxy-17β-cyano-Δ$^9$-estrene-5α-ol-3-one with a specific rotation of $[\alpha]_D^{20} = -58° \pm 2.5°$ (c=0.4% in CHCl$_3$) and melting at 136° C.

EXAMPLE 7

Using the procedure of Example 1, p-methoxyphenyl magnesium bromide was reacted with the said acetal to obtain a 92% yield of 3-[(1,2-ethanediyl)-acetal] of 11β-(p-methoxyphenyl)-17α-trimethylsilyloxy-17β-cyano-Δ$^9$-estrene-5α-ol-3-one melting at 210° C. and having a specific rotation of $[\alpha]_D^{20} = -12° \pm 2°$ (c=0.4% in CHCl$_3$).

EXAMPLE 8

Using the procedure of Example 1, benzyl magnesium bromide was reacted with the said acetal to obtain a 94% yield of 3-[(1,2-ethanediyl)-acetal] of 11β-benzyl-17α-trimethylsilyloxy-17β-cyano-Δ$^9$-estrene-5α-ol-3-one melting at 160° C. and having a specific rotation of $[\alpha]_D^{20} = -86° \pm 3°$ (c=0.3% in CHCl$_3$).

EXAMPLE 9

Using the procedure of Example 1, 2-thienyl magnesium bromide was reacted with the said acetal to obtain a 92% yield of 3-[(1,2-ethanediyl)-acetal] of 11β-(2-thienyl)-17α-trimethylsilyloxy-17β-cyano-Δ$^9$-estrene-5α-ol-3-one melting at 260° C. and having a specific rotation of $[\alpha]_D^{20} = +34° \pm 2.5°$ (c=0.4% in CHCl$_3$).

EXAMPLE 10

4.6 ml of a solution of 2.2 M of dimethyllithium in ether were added at 0° C. to a suspension of 955 mg of cuprous iodide in 5 ml of ether and then a solution of 436 mg of 3-[(1,2-ethanediyl)-acetal] of 5α,10α-epoxy- 17β-benzoyloxy-Δ$^{9(11)}$-estrene-3-one in 2 ml of tetrahydrofuran were added thereto. The mixture was stirred at 0° C. for 35 minutes and was then poured into aqueous ammonium chloride solution. The mixture was extracted with ether and the ether extracts were dried and evaporated to dryness to obtain 460 mg of 3-[(1,2-ethanediyl)-acetal] of 11β-methyl-17β-benzoyloxy-Δ$^9$-estrene-5α-ol-3-one.

RMN Spectrum (60 MHz): 18—CH$_3$—67 Hz; 11—CH$_3$—63 to 71 Hz; 11—H—180 Hz.

EXAMPLE 11

Using the procedure of Example 10, lithium diethyl cuprate and 3-[(1,2-ethanediyl)-acetal] of 5α,10α-epoxy-17α-trimethylsilyloxy-17β-cyano-Δ$^{9(11)}$-estrene-3-one were reacted to obtain a 100% yield of 3-[(1,2-ethanediyl)-acetal] of 11β-ethyl-17α-trimethylsilyloxy-17β-cyano-Δ$^9$-estrene-5α-ol-3-one with a specific rotation of $[α]_D^{20}= -61°±2.5°$ (c=0.5% in CHCl$_3$).

EXAMPLE 12

Using the procedure of Example 10, lithium diphenyl cuprate and 3-[(1,2-ethanediyl)-acetal] of 5α,10α-epoxy-17α-trimethylsilyloxy-17β-cyano-Δ$^{9(11)}$-estrene-3-one were reacted to obtain a 98.6% yield of 3-[(1,2-ethanediyl)-acetal] of 11β-phenyl-17α-trimethylsilyloxy-17β-cyano-Δ$^9$-estrene-5α-ol-3-one with a melting point of 186° C. and a specific rotation of $[α]_D^{20}= -12.5°±2°$ (c=0.6% in CHCl$_3$).

EXAMPLE 13

Using the procedure of Example 10, lithium diphenyl cuprate and 3-[(1,2-ethanediyl)-acetal] of 5α,10α-epoxy-17β-benzoyloxy-Δ$^{9(11)}$-estrene-3-one were reacted to obtain a 70% yield of 3-[(1,2-ethanediyl)-acetal] of 11β-phenyl-17β-benzoyloxy-Δ$^9$-estrene-5α-ol-3-one melting at 188° C. and having a specific rotation of $[α]_D^{20}= +12°+2°$ (c=0.45% in CHCl$_3$).

EXAMPLE 14

Using the procedure of Example 10, lithium dimethyl cuprate and 3,17-di-[(1,2-ethanediyl)-acetal] of 5α,10α-epoxy-Δ$^{9(11)}$-estrene-3,17-dione were reacted to obtain a 90% yield of 3,17-di-[(1,2-ethanediyl)-acetal] of 11β-methyl-Δ$^9$-estrene-5α-ol-3,17-dione melting at 122° C. and having a specific rotation of $[α]_D^{20}= -86.5°±2°$ (c=1% in CHCl$_3$).

EXAMPLE 15

6 ml of tert.-butyllithium were added at −50° C. to a suspension of 0.81 g of a dimethyl sulfide-cuprous bromide complex in 5 ml of tetrahydrofuran and 10 ml of tetrahydrofuran were then added thereto. After 15 minutes, a solution of 0.840 g of 3-[(1,2-ethanediyl)-acetal] of 5α,10α-epoxy-17α-trimethylsilyloxy-17β-cyano-Δ$^{9(11)}$-estrene-3-one in 10 ml of tetrahydrofuran were added thereto. The reaction mixture was kept at −25° C. for 16 hours and was poured into aqueous ammonium chloride solution. The mixture was extracted with ether and the ether extracts were dried and evaporated to dryness to obtain a 0.942 g of 3-[(1,2-ethanediyl)-acetal] of 11β-tert.-butyl-17α-trimethylsilyloxy-17β-cyano-Δ$^9$-estrene-5α-ol-3-one with a specific rotation of $[α]_D^{20}= -58°±3°$ (c=0.3% in CHCl$_3$).

EXAMPLE 16

A solution of 1.8 g of methoxy ethylene in 10 ml of tetrahydrofuran was added at −70° C. to 16 ml of a solution of 0.88 M of tert.-butyllithium in tetrahydrofuran and the solution was held at −10° C. for 30 minutes to obtain a solution of methoxy vinyl lithium. The said solution was added at −40° C. to a suspension of 1.4 g of a dimethyl sulfide-cuprous bromide complex in 5 ml of tetrahydrofuran and then a solution of 1.3 g of 3-[(1,2-ethanediyl)-acetal] of 5α,10α-epoxy-17α-trimethylsilyloxy-17β-cyano-Δ$^{9(11)}$-estrene-3-one in 5 ml of tetrahydrofuran was added thereto. The mixture was held at −10° C. for 90 minutes and was then poured into an aqueous ammonium chloride solution. The mixture was extracted with ether and the ether extracts were dried and evaporated to dryness to obtain 1.3 g of 3-[(1,2-ethanediyl)-acetal] of 11β-methoxyvinyl-17α-trimethylsilyloxy-17β-cyano-Δ$^9$-estrene-5α-ol-3-one with a specific rotation of $[α]_D^{20}= -56°±2°$ (c=0.4% in CHCl$_3$).

EXAMPLE 17

A solution of 26.8 g of allyl phenyl ether in 75 ml of ether was added at −15° C. to a suspension of 5.6 g of lithium in 150 ml of tetrahydrofuran to obtain a solution of allyllithium and 83 ml of the said solution were added at −78° C. to a suspension of 5.15 g of a dimethyl sulfide-cuprous bromide complex in 20 ml of tetrahydrofuran. After 15 minutes at −70° C., a solution of 3-[(1,2-ethanediyl)-acetal] of 5α,10α-epoxy-17α-trimethylsilyloxy-17β-cyano-Δ$^{9(11)}$-estrene-3-one in 20 ml of tetrahydrofuran was added thereto and after 30 minutes, the mixture was poured into an aqueous ammonium chloride solution. The mixture was extracted with ether and the ether extracts were dried and evaporated to dryness to obtain 4.2 g of 3-[(1,2-ethanediyl)-acetal] of 11β-allyl-17α-trimethylsilyloxy-17β-cyano-Δ$^9$-estrene-5α-ol-3-one with a specific rotation of $[α]_D^{20}= -52°±2°$ (c=0.6% in CHCl$_3$).

EXAMPLE 18

Using the procedure of Example 1, o-methoxyphenyl magnesium bromide and 3-[(1,2-ethanediyl)-acetal] of 5α,10α-epoxy-17α-trimethylsilyloxy-17β-cyano-Δ$^{9(11)}$-estrene-3-one were reacted to obtain an 86% yield of 3-[(1,2-ethanediyl)-acetal] of 11β-(o-methoxyphenyl)-17α-trimethylsilyloxy-17β-cyano-Δ$^9$-estrene-5α-ol-3-one with a specific rotation of $[α]_D^{20}= -16.5°±1°$ (c=0.55% in CHCl$_3$).

EXAMPLE 19

Using the procedure of Example 1, p-fluorophenyl magnesium bromide and 3-[(1,2-ethanediyl)-acetal] of 5α,10α-epoxy-17α-trimethylsilyloxy-17β-cyano-Δ$^{9(11)}$-estrene-3-one were reacted to obtain a 90% yield of 3-[(1,2-ethanediyl-acetal] of 11β-(p-fluorophenyl)-17α-trimethylsilyloxy-17β-cyano-Δ$^9$-estrene-5α-ol-3-one melting point of 166° C. and specification of $[α]_D^{20}= -7.5°±2°$ (c=0.5% in CHCl$_3$).

EXAMPLE 20

A few drops of pyridine and 22 ml of a solution of 0.75 M of hexafluoroacetone hydroperoxide were added at 0° C. to a solution of 4.68 g of 3-[(1,2-ethanediyl)-acetal] of 18-methyl-Δ$^{5(10),9(11)}$-estradiene-17β-ol-3-one (prepared by process of Belgium Pat. No. 632,347) in 200 ml of methylene chloride and the mix ture was stirred for 30 minutes and was then poured into an aqueous sodium bicarbonate-sodium thiosulfate solution. The mixture was extracted with ether and the ether extracts were evaporated to dryness to obtain 2 g of 3-[(1,2-ethanediyl)-acetal] of 5α,10α-epoxy-18-methyl-Δ$^{9(11)}$-estrene-17β-ol-3-one. 1.5 g of the said product and 16 ml of a solution of vinyl magnesium bromide in tetrahydrofuran were reacted as in Example 1 to obtain 0.98 g of 3-[(1,2-ethanediyl)-acetal] of 11β-vinyl-18-methyl-Δ$^9$-estrene-5α,17β-diol-3-one.

EXAMPLE 21

14 ml of a solution of 0.43 M of ethyllithium in ether were added at −20° C. to a suspension of 570 mg of cuprous iodide in ether and then 872 mg of 3-[(1,2-ethanediyl)-acetal] of 5α,10α-epoxy-17β-benzoyloxy-Δ$^{9(11)}$-estrene-3-one were added thereto. The temperature was allowed to rise to 0° C. and the mixture was then poured into an aqueous ammonium chloride solution. The mixture was extracted with ether and the ether extracts were dried and evaporated to dryness to obtain 966 mg of 3-[(1,2-ethanediyl)-acetal] of 11β-ethyl-17β-benzoyloxy-Δ$^9$-estrene-5α-ol-3-one.

EXAMPLE 22

10 g of 3-[(1,2-ethanediyl)-acetal] of 17α-methyl-17β-acetyl-Δ$^{5(10),9(11)}$-estradiene-3-one (prepared by French Pat. No. 2,149,302) were added to a solution of 0.5 ml of pyridine in 240 ml of methylene chloride and after cooling the mixture to 0° C., 40 ml of a hexafluoroacetone hydroperoxyde solution (30 mm) were added thereto. After 10 minutes, the mixture was poured into an aqueous sodium thiosulfate-sodium bicarbonate solution and the mixture was extracted with methylene chloride. The organic extracts were dried and evaporated to dryness and the residue was crystallized from isopropyl ether to obtain 8.2 g of 3-[(1,2-ethanediyl)-acetal] of 5α,10α-epoxy-17α-methyl-17β-acetyl-Δ$^{9(11)}$-estrene-3-one.

A solution of 4 g of the said acetal in 15 ml of tetrahydrofuran was added at −40° C. to a solution of 150 mg of cuprous chloride in 17.6 ml of a solution of vinyl magnesium bromide and after standing 2 hours at −40° C., the mixture was poured into an aqueous ammonium chloride solution. The mixture was extracted with ether and the ether extracts were dried and evaporated to dryness. The residue was crystallized from isopropyl ether to obtain 2.68 g of 3-[(1,2-ethanediyl)-acetal] of 11β-vinyl-17α-methyl-17β-acetyl-Δ$^9$-estrene-5α-ol-3-one.

EXAMPLE 23

2 g of a lithium acetylide-ethylenediamine complex were added to a solution of 2.3 g of 3-[(1,2-ethanediyl)-acetal] of 11β-ethyl-17α-trimethylsilyloxy-17β-cyano-Δ$^9$-estrene-5α-ol-3-one in 50 ml of ethylenediamine and the mixture was stirred at room temperature for 19 hours. Another 2 g of the said complex were added to the mixture which was stirred at room temperature for 1 hour, at 45° C. for 105 minutes and at room temperature for 15 hours. Another 1 g of the said complex were added thereto and the mixture was heated at 45° C. for 1 hour after which another 1 g of the complex was added thereto. The mixture was heated at 40° C. for 30 minutes and was then poured into ice water. The mixture was extracted with ether and the ether extracts were dried and evaporated to dryness to obtain 3-[(1,2-ethanediyl)-acetal] of 11β-ethyl-17α-ethynyl-Δ$^9$-estrene-5α,17β-diol-3-one.

EXAMPLES 24 to 33

Using the procedure of Example 23, the acetals of Table I were reacted to form the Δ$^9$-estrenes of Table I.

TABLE I

| EXAMPLE | STARTING PRODUCT | FINAL PRODUCT |
|---|---|---|
| 24 | 3-[(1,2-ethanediyl)-acetal] of 11β-propyl-17β-cyano-17α-trimethylsilyloxy-Δ$^9$-estrene-5α-ol-3-one | 3-[(1,2-ethanediyl)-acetal] of 11β-propyl-17α-ethynyl-Δ$^9$-estrene-5α,17β-diol-3-one melting at 170° C. |
| 25 | 3-[(1,2-ethanediyl)-acetal] of 11β-isopropyl-17β-cyano-17α-trimethylsilyloxy-Δ$^9$-estrene-5α-ol-3-one | 3-[(1,2-ethanediyl)-acetal] of 11β-isopropyl-17α-ethynyl-Δ$^9$-estrene-5α,17β-diol-3-one melting at 175° C. |
| 26 | 3-[(1,2-ethanediyl)-acetal] of 11β-decyl-17β-cyano-17α-trimethylsilyloxy-Δ$^9$-estrene-5α-ol-3-one | 3-[(1,2-ethanediyl)-acetal] of 11β-decyl-17α-ethynyl-Δ$^9$-estrene-5α,17β-diol-3-one with an Rf = 0.27 (petroleum ether-ethyl acetate 6-4) |
| 27 | 3-[(1,2-ethanediyl)-acetal] of 11β-vinyl-17β-cyano-17α-trimethylsilyloxy-Δ$^9$-estrene-5α-ol-3-one | 3-[(1,2-ethanediyl)-acetal] of 11β-vinyl-17α-ethynyl-Δ$^9$-estrene-5α,17β-diol-3-one melting at 160° C. |
| 28 | 3-[(1,2-ethanedlyl)-acetal] of 11β-isopropenyl-17β-cyano-17α-trimethylsilyloxy-Δ$^9$-estrene-5α-ol-3-one | 3-[(1,2-ethanediyl)-acetal] of 11β-isopropenyl-17α-ethynyl-Δ$^9$-estrene-5α, 17β-diol-3-one melting at 193° C. |
| 29 | 3-[(1,2-ethanediyl)-acetal] of 11β-allyl-17β-cyano-17α-trimethylsilyloxy-Δ$^9$-estrene-5α-ol-3-one | 3-[(1,2-ethanediyl)-acetal] of 11β-allyl-17α-ethynyl-Δ$^9$-estrene-5α,17β-diol-3-one |
| 30 | 3-[(1,2-ethanediyl)-acetal] of 11β-benzyl-17β-cyano-17α-trimethylsilyloxy-Δ$^9$-estrene-5α-estrene-5α,17β-diol-3-one ol-3-one | 3-[(1,2-ethanediyl)-acetal] of 11β-benzyl-17α-ethynyl-Δ$^9$- melting at 152° C. |
| 31 | 3-[(1,2-ethanediyl)-acetal] of 11β-(p-methoxyphenyl)-17β-cyano-17α-trimethylsilyloxy-Δ$^9$-estrene-5α-ol-3-one | 3-[(1,2-ethanediyl)-acetal] of 11β-(p-methoxyphenyl)-17α-ethynyl-Δ$^9$-estrene-5α,17β-diol-3-one melting at 150° C. |
| 32 | 3-[(1,2-ethanedlyl)-acetal] of 11β-(2-thienyl)-17β-cyano-17α-trimethylsilyloxy-Δ$^9$-estrene-5α-ol-3-one | 3-[(1,2-ethanedlyl)-acetal] of 11β-(2-thienyl)-17α-ethynyl-Δ$^9$-estrene-5α,17β-diol-3-one melting at 140° C. |

TABLE I-continued

| EXAMPLE | STARTING PRODUCT | FINAL PRODUCT |
|---------|------------------|---------------|
| 33 | 3-[(1,2-ethanediyl)-acetal-] of 11β-(o-methoxyphenyl)-17β-cyano-17α-trimethylsilyloxy-Δ$^9$-estrene-5α-ol-3-one | 3-[(1,2-ethanediyl)-acetal] of 11β-(o-methoxyphenyl)-17α-ethynyl-Δ$^9$-estrene-5α,17β-diol-3-one |

EXAMPLE 34

1 g of 3-[(1,2-ethanediyl)-acetal] of 11β-ethyl-17β-cyano-17α-trimethylsilyloxy-Δ$^9$-estrene-5α-ol-3-one was added to 8.8 ml of a solution of 0.98 M of methyl magnesium bromide in tetrahydrofuran and the mixture was refluxed for 19 hours and was then poured into an aqueous ammonium chloride solution. The mixture was extracted with methylene chloride and the organic extracts were dried and evaporated to dryness to obtain 904 mg of 3-[(1,2-ethanediyl)-acetal] of 11β-ethyl-17β-acetyl-Δ$^9$-estrene-5α,17β-diol-3-one melting at 166°~168° C.

EXAMPLE 35

7 ml of 0.98 M of methyl magnesium bromide in tetrahydrofuran were concentrated by distilling off 3.9 ml of tetrahydrofuran and then 240 mg of 3-[(1,2-ethanediyl)-acetal] of 11β-phenyl-17β-cyano-17α-trimethylsilyloxy-Δ$^9$-estrene-5α-ol-3-one were added thereto. The mixture was refluxed for 5½ hours and was then poured into an aqueous ammonium chloride solution. The mixture was extracted with methylene chloride and the organic extracts were dried and evaporated to dryness to obtain 252 mg of 3-[(1,2-ethanediyl)-acetal] of 11β-phenyl-17β-acetyl-Δ$^9$-estrene-5α,17α-diol-3-one melting at 159°–162° C.

EXAMPLE 36

1.4 g of 3-[(1,2-ethanediyl)-acetal] of 11β-vinyl-17β-cyano-17α-trimethylsilyloxy-Δ$^9$-estrene-5α-ol-3-one were added to 16 ml of a 2M solution of methyl magnesium bromide in tetrahydrofuran and the mixture was refluxed for 17 hours and was poured into an aqueous ammonium chloride solution. The mixture was extracted with ether and the ether extracts were evaporated to dryness to obtain 3-[(1,2-ethanediyl)-acetal] of 11β-vinyl-17β-acetyl-Δ$^9$-estrene-5α,17α-diol-3-one.

EXAMPLE 37

30 mg of cuprous chloride were added at −70° C. to 3 ml of a solution of 1.45 M of methyllithium in ether and after stirring the mixture for 15 minutes, a solution of 0.86 g of 3-[(1,2-ethanediyl)-acetal] of 5α,10α-epoxy-17α-trimethylsilyloxy-17β-cyano-Δ$^{9(11)}$-estrene-3-one in 5 ml of tetrahydrofuran was added thereto. The mixture was stirred at −70° C. for 30 minutes and then at −30° C. for 1 hour and at 10° C. for 2 hours. The mixture was poured into an aqueous ammonium chloride solution and the mixture was extracted with ether. The ether extracts were dried and evaporated to dryness and the residue was chromatographed over silica gel. Elution with a 7-3 benzene-ethyl acetate mixture yielded 3-[(1,2-ethanediyl)-acetal] of 11β-methyl-17α-trimethylsilyloxy-17β-cyano-Δ$^9$-estrene-5α-ol-3-one melting at 165° C. and having a specific rotation of $[\alpha]_D^{20} = -54°\pm2.5°$ (c=0.5% in CHCl$_3$).

RMN Spectrum (CDCl$_3$): 18—CH$_3$—64 Hz; 11—CH$_3$—64 to 71.5 Hz; 11—H—192 Hz; ketal—240 Hz; —OH—257 Hz; —SiMe$_3$—12.5 Hz.

EXAMPLE 38

5 ml of sodium hydroxide were added to a solution of 1.5 g of 3-[(1,2-ethanediyl)-acetal] of 11β-propyl-17α-trimethylsilyloxy-17β-cyano-Δ$^9$-estrene-5α-ol-3-one in 50 ml of ethanol and the mixture was stirred for 30 minutes at 20° C. and was then poured into water. The mixture was extracted with ether and the ether extracts were dried and evaporated to dryness. The residue was taken up in 5 ml of tetrahydrofuran and 30 ml of a solution of 1 M methyl magnesium bromide in tetrahydrofuran was added thereto. The mixture was refluxed for 8 hours and was then concentrated. The temperature was held at 20° C. for 15 hours and the mixture was poured into aqueous ammonium chloride solution. The mixture was extracted with ether and the ether extracts were dried and evaporated to dryness. The residue was treated a second time with magnesium as above to obtain 1.3 g of 3-[(1,2-ethanediyl)-acetal] of 11β-propyl-17α-methyl-Δ$^9$-estrene-5α,17β-diol-3-one.

EXAMPLES 39 TO 46

Using the procedure of Example 38 the acetals of Table II were reacted to obtain the final products listed therein.

| EXAMPLE | STARTING ACETAL | FINAL PRODUCT |
|---------|-----------------|---------------|
| 39 | 3-[(1,2-ethanediyl-acetal] of 11β-isopropyl-17α-trimethylsilyloxy-17β-cyano-Δ$^9$-estrene-5α-ol-3-one | 3-[(1,2-ethanediyl)-acetal] of 11β-isopropyl-17α-methyl-Δ$^9$-estrene-5α,17β-diol-3-one |
| 40 | 3-[(1,2-ethanediyl)-acetal] of 11β-decyl-17α-trimethylsilyloxy-17β-cyano-Δ$^9$-estrene-5α-ol-3-one | 3-[(1,2-ethanediyl)-acetal] of 11β-decyl-17α-methyl-Δ$^9$-estrene-5α,17β-diol-3-one |
| 41 | 3-[(1,2-ethanediyl)-acetal] of 11β-isopropenyl-17α-trimethylsilyloxy-17β-cyano-Δ$^9$-estrene-5α-ol-3-one | 3-[(1,2-ethanediyl)-acetal] of 11β-isopropenyl-17α-methyl-Δ$^9$-estrene-5α,17β-diol-3-one |
| 42 | 3-[(1,2-ethanediyl)-acetal] of 11β-allyl-17α-trimethylsilyloxy-17β-cyano-Δ$^9$-estrene-5α-ol-3-one | 3-[(1,2-ethanediyl)-acetal] of 11β-allyl-17α-methyl-Δ$^9$-estrene-5α,17β-diol-3-one |
| 43 | 3-[(1,2-ethanediyl)-acetal] of 11β-vinyl-17α-trimethylsilyloxy-17β-cyano-Δ$^9$-estrene-5α-ol | 3-[(1,2-ethanediyl)-acetal] of 11β-vinyl-17α-methyl-Δ$^9$-estrene-5α,17β-diol-3-one |

-continued

| EXAMPLE | STARTING ACETAL | FINAL PRODUCT |
| --- | --- | --- |
| | -3-one | |
| 44 | 3-[(1,2-ethanediyl)-acetal] of 11β-(p-methoxyphenyl)-17α-trimethylsilyloxy-17β-cyano-Δ⁹-estrene-5α-ol-3-one | 3-[(1,2-ethanediyl)acetal-] of 11β-(p-methoxyphenyl)-17α-methyl-Δ⁹-estrene-5α,17β-diol-3-one |
| 45 | 3-[(1,2-ethanediyl)-acetal] of 11β-benzyl-17α-trimethylsilyloxy-17β-cyano-Δ⁹-estrene-5α-ol-3-one | 3-[(1,2-ethanediyl)-acetal] of 11β-benzyl-17α-methyl-Δ⁹-estrene-5α,17β-diol-3-one |
| 46 | 3-[(1,2-ethanediyl)-acetal] of 11β-(2-thienyl)-17α-trimethylsilyloxy-17β-cyano-Δ⁹-estrene-5α-ol-3-one | 3-[(1,2-ethanediyl)-acetal] of 11β-(2-thienyl)-17α-methyl -Δ⁹-estrene-5α,17α-diol-3-one. |

EXAMPLE 47

1.6 g of Redex CF (sulfonic acid resin) was added to a solution of the product of Example 22 in 95% ethanol and the mixture was refluxed for 1 hour and was filtered. The filtrate was evaporated to dryness under reduced pressure and the residue was crystallized from isopropyl ether to obtain 955 mg of 11β-ethyl-17α-ethynyl-Δ$^{4,9}$-estradiene-17β-ol-3-one melting at 177° C. and having a specific rotation of $[\alpha]_D^{20} = -202° \pm 4°$ (c=0.47% in CHCl$_3$).

230 mg of the product was dissolved in 0° C. in 1.5 ml of methylene chloride and 0.25 ml of acetic anhydride and 0.125 ml of acetyl bromide were added thereto. The temperature was allowed to return to room temperature and the mixture was stirred for 1 hour and was then poured into an aqueous sodium bicarbonate solution. The mixture was extracted with chloroform and the organic extracts were dried over sodium sulfate and evaporated to dryness. The residue was dissolved in 12.5 ml of methanol and 1 ml of sodium hydroxide solution was added thereto. The mixture was held at room temperature for 105 minutes and was poured into water. The mixture was acidified with concentrated sulfuric acid and was extracted with methylene chloride. The organic extracts were evaporated to dryness and the residue was chromatographed over silica gel. Elution with a 7-3 benzene-ethyl acetate mixture yielded 1.75 mg of 11β-ethyl-17α-ethynyl-Δ$^{1,3,5(10)}$-estratriene-3,17β-diol with a specific rotation of $[\alpha]_D^{20} = +84.6° \pm 2°$ (c=0.5% in CHCl$_3$).

EXAMPLE 48

Using the procedure of Example 10, a solution of methyllithium and cuprous iodide and 3,3-dimethylketal-5α,10α-epoxy-Δ$^{9(11)}$-estrene-3,17-dione were reacted to obtain 3,3-dimethylketal-11β-methyl-Δ⁹-estrene-5α-ol-3,17-dione.

Various modifications of the products and process of the invention may be made without departing from the spirit or scope thereof and it is to be understood that the invention is intended to be limited only as defined in the appended claims.

I claim:

1. A compound having the formula

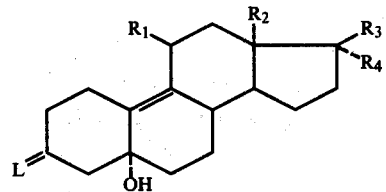

wherein L is a ketal, R$_1$ is selected from the group consisting of branched and straight chain alkyl of 1 to 12 carbon atoms, unsaturated alkyl of 2 to 8 carbon atoms optionally substituted with a member selected from the group alkoxy and alkylthio of 1 to 4 carbon atoms and halogens, aryl of 6 to 12 carbon atoms and aralkyl of 7 to 13 carbon atoms optionally substituted with a member selected from the group consisting of alkoxy and alkylthio of 1 to 4 carbon atoms and halogens, thienyl, isothienyl and furyl, R$_2$ is alkyl of 1 to 4 carbon atoms and R$_3$ is selected from the group consisting of hydrogen, hydroxy, acyloxy of an organic carboxylic acid of 1 to 18 carbon atoms, alkoxy of 1 to 8 carbon atoms and acyl of an organic carboxylic acid of 1 to 18 carbon atoms and R$_4$ is selected from the group consisting of hydrogen, hydroxy, alkyl and alkxoy of 1 to 8 carbon atoms, alkenyl and alkynyl of 2 to 8 carbon atoms, acyloxy of an organic carboxylic acid of 1 to 18 carbon atoms and cyano, or one of R$_3$ and R$_4$ is a blocked hydroxy in the form of an easily removable ether and the other is cyano, or R$_3$ and R$_4$ form a ketone optionally protected as a cyclic ketal.

2. A compound of claim 1 wherein L is ethyleneketal.

3. A compound of claim 1 having the formula

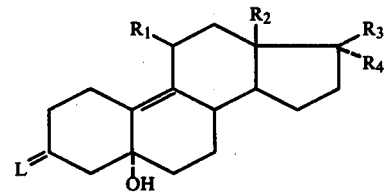

wherein L is a ketal and R$_3$ is selected from the group consisting of hydrogen, hydroxy, acyloxy of an organic carboxylic acid of 1 to 18 carbon atoms, alkoxy of 1 to 8 carbon atoms, and acyl of an organic carboxylic acid of 1 to 18 carbon atoms and R$_4$ is selected from the group consisting of hydrogen, hydroxy, alkyl and alkoxy of 1 to 8 carbon atoms, alkenyl and alkynyl of 2 to 8 carbon atoms, acyloxy of an organic carboxylic acid of 1 to 18 carbon atoms and cyano or one of R$_3$ and R$_4$ is a blocked hydroxy in the form of an easily removable ether and the other is cyano.

4. A compound of claim 1 wherein $R_2$ is methyl.

5. A compound of claim 1 wherein $R_2$ is ethyl.

6. A compound of claim 1 wherein $R_3$ is benzoyloxy and $R_4$ is hydrogen.

7. A compound of claim 1 wherein $R_3$ is cyano and $R_4$ is trimethylsilyloxy.

8. A compound of claim 1 wherein $R_1$ is alkyl of 1 to 12 carbon atoms.

9. A compound of claim 1 wherein $R_1$ is an unsaturated alkyl of 2 to 4 carbon atoms optionally substituted with alkoxy or alkylthio of 1 to 4 carbon atoms or at least one fluorine.

10. A compound of claim 1 wherein $R_1$ is selected from the group consisting of phenyl and benzyl optionally substituted on the phenyl with at least one member of the group consisting of halogen, alkyl of 1 to 4 carbon atoms, alkoxy of 1 to 4 carbon atoms and $-CF_3$.

11. A compound of claim 1 wherein $R_1$ is thienyl.

12. A process for the preparation of a compound of claim 1 comprising reacting a compound of the formula

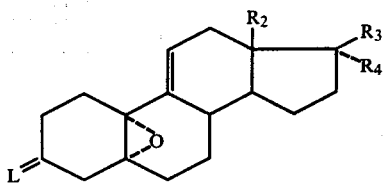

wherein L is a ketal and $R_3$ is selected from the group consisting of hydrogen, hydroxy, acyloxy of an organic carboxylic acid of 1 to 18 carbon atoms, alkoxy of 1 to 8 carbon atoms and acyl of an organic carboxylic acid of 1 to 18 carbon atoms and $R_4$ is selected from the group consisting of hydrogen, hydroxy, alkyl and alkoxy of 1 to 8 carbon atoms, alkenyl and alkynyl of 2 to 8 carbon atoms, acyloxy of an organic carboxylic acid of 1 to 18 carbon atoms and cyano, or one of $R_3$ and $R_4$ is a blocked hydroxy in the form of an easily removable ether and the other is cyano, or $R_3$ and $R_4$ form a ketone optionally protected as a cyclic ketal with a compound of a formula selected from the group consisting of $(R_1)_2$ CuLi, $R_1$ MgHal and $R_1$ Li wherein $R_1$ has the above definition and Hal is a halogen in the presence of a catalytic amount of a cuprous halide when $R_1$ Mg Hal and $R_1$ Li are used.

13. The process of claim 12 wherein $R_3$ and $R_4$ are other than a ketone optionally protected as a ketal.

* * * * *